United States Patent
Muddasani et al.

(10) Patent No.: US 8,759,582 B2
(45) Date of Patent: Jun. 24, 2014

(54) PROCESS FOR THE PREPARATION OF LACOSAMIDE

(75) Inventors: Pulla Reddy Muddasani, Hyderabad (IN); Veerababu Madalapu, Hyderabad (IN); Venkaiah Chowdary Nannapaneni, Hyderabad (IN)

(73) Assignee: Natco Pharma Limited, Andhra Pradesh (IN)

( * ) Notice: Subject to any disclaimer, the term of this patent is extended or adjusted under 35 U.S.C. 154(b) by 134 days.

(21) Appl. No.: 13/577,367

(22) PCT Filed: Feb. 4, 2011

(86) PCT No.: PCT/IN2011/000082
§ 371 (c)(1),
(2), (4) Date: Oct. 17, 2012

(87) PCT Pub. No.: WO2011/095995
PCT Pub. Date: Aug. 11, 2011

(65) Prior Publication Data
US 2013/0035508 A1   Feb. 7, 2013

(30) Foreign Application Priority Data

Feb. 8, 2010   (IN) .............................. 314/CHE/2010

(51) Int. Cl.
   *C07C 233/05* (2006.01)
   *C07C 231/02* (2006.01)
   *C07C 231/08* (2006.01)

(52) U.S. Cl.
   USPC ...................................................... 564/158

(58) Field of Classification Search
   USPC ...................................................... 564/158
   See application file for complete search history.

(56) References Cited

U.S. PATENT DOCUMENTS

| 5,773,475 | A | 6/1998 | Kohn |
| 2008/0027137 | A1 | 1/2008 | Riedner et al. |
| 2009/0143472 | A1 | 6/2009 | Madhra et al. |

FOREIGN PATENT DOCUMENTS

| CN | 101591300 | 12/2009 |
| WO | 97/33861 A1 | 9/1997 |
| WO | 2006/037574 A1 | 4/2006 |

OTHER PUBLICATIONS

Albeck et al., "Peptidyl Epoxides: Novel Selective Inactivators of Cysteine Proteases," J. Am. Chem. Soc., 1996, vol. 118, pp. 3591-3596.
Andurkar et al., "Synthesis and anticonvulsant activities of (R)-(O)-methylserine derivatives," Tetrahedron: Asymmetry, 1998, vol. 9, pp. 3841-3854.
Choi et al., "Synthesis and Anticonvulsant Activities of N-Benzyl-2-acetamidopropionamide Derivatives," J. Med. Chem., 1996, vol. 39, pp. 1907-1916.
Keller et al., "*tert*-Butoxycarbonylation of Amino Acids and Their Derivatives: N-*tert*-Butoxycarbonyl-l-phenylalanine," Organic Syntheses, Coll., 1990, vol. 7, p. 70.
Morieux et al., "Synthesis and anticonvulsant activities of N-benzyl (2R)-2-acetamido-3-oxysubstituted propionamide derivatives," Bioorganic & Medicinal Chemistry, 2008, vol. 16, pp. 8968-8975.
Yin-Ling et al., "Synthesis of Lacosamide," Chinese Journal of Pharmaceuticals, 2009, vol. 40, pp. 641-643.
IPCOM # 000181080D, "Novel Intermediate Compounds and Their Use in Preparation of Lacosamide," IP.com Electronic Publication Mar. 25, 2009, 25 pages.

*Primary Examiner* — Shailendra Kumar
(74) *Attorney, Agent, or Firm* — Kilpatrick Townsend & Stockton LLP

(57) ABSTRACT

Present invention relates to an improved and commercial process for the preparation of lacosamide ((R)-2-acetamido-N-benzyl-3-methoxypropanamide) of formula (I). Present process utilizes high purity crystalline solids of formulae (XXXII) and (XIII) as key intermediates. Lacosamide is indicated for the adjunctive treatment of partial onset seizures in patients aged at least 17 years.

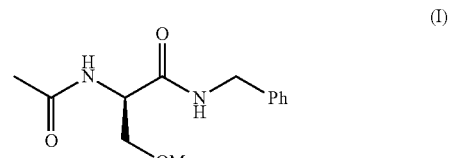

(I)

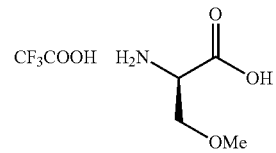

(XXXII)

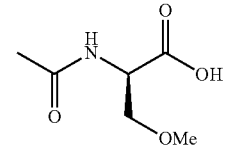

(XIII)

11 Claims, No Drawings

PROCESS FOR THE PREPARATION OF LACOSAMIDE

This application is a U.S. National Phase under 35 USC 371 of PCT Application No. PCT/IN2011/000082 filed Feb. 4, 2011, which claims priority to India Application No. 314/CHE/2010, filed Feb. 8, 2010, the disclosures of which are incorporated by reference herein.

FIELD OF INVENTION

Present invention relates to an improved and commercial process for the preparation of lacosamide ((R)-2-acetamido-N-benzyl-3-methoxypropanamide) of formula-I

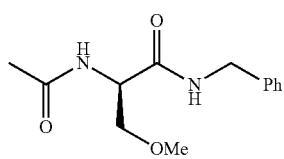

Lacosamide is an amino acid derivative having analgesic and anticonvulsant property. Schwarz Pharma (a subsidiary of UCB), under license from Harris FRC, has developed and launched oral (tablet and syrup) lacosamide (Vimpat; formerly known as harkoseride and erlosamide). Lacosamide acts as sodium channel modulator; analgesic; dihydropyrimidinase related protein 2 modulator; anticonvulsant agent. The product is indicated for the adjunctive treatment of partial onset seizures in patients aged at least 17 years. An iv infusion formulation of lacosamide is also available. It was approved by US FDA as an adjunctive therapy for partial-onset seizures in Oct. 2008.

BACKGROUND OF INVENTION

Lacosamide is reported for the first time in WO9733861 (corresponding U.S. Pat. No. 5,773,475) by Research Corporation Technologies, USA. It is also published in J. Med. Chem. 1996, 39, 1907-1916. According to this literature, lacosamide can be made in three routes. According to one route (Scheme-I), D-serine is converted to methyl ester and reacted with benzyl amine to get the

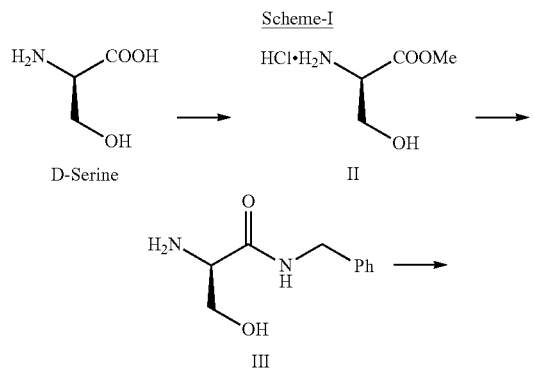

corresponding benzylamide. This intermediate is reacted with acetic anhydride to get the N-acetyl derivative. Methylation using methyl iodide in the presence of silver (I) oxide gave lacosamide. Overall yield of lacosamide by this route is 6.9%. This route is not commercially viable due to low yield and usage of costly reagent like silver oxide.

According to another route (Scheme-II) D-serine is reacted with acetic anhydride to get the corresponding N-acetyl derivative. This intermediate is reacted with benzylamine to get the corresponding benzylamide derivative which on methylation using methyl iodide and silver (I) oxide gave lacosamide. Overall yield of lacosamide by this route is 28.7%. This route is not commercially viable as it requires column chromatography in the amide intermediate (IV) isolation stage.

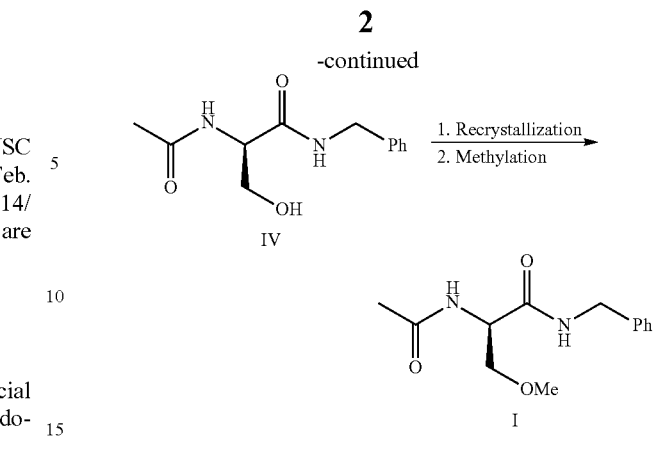

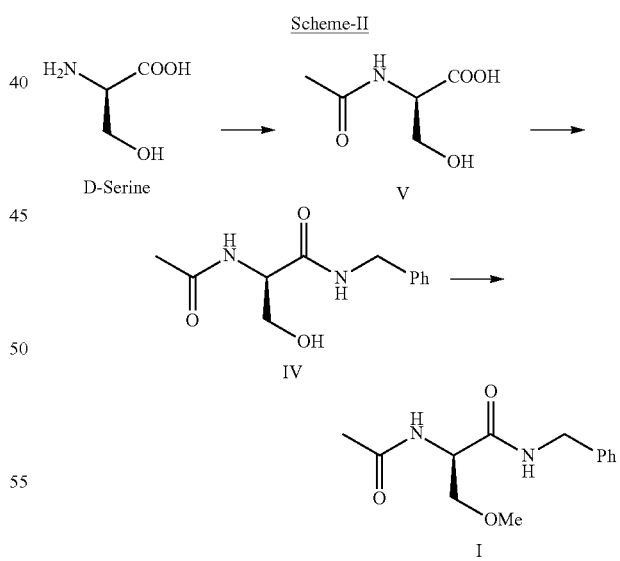

According to one more route described in the above reference, amino group of D-serine is protected by benzyl chloroformate and reacted with methyl iodide in the presence of silver oxide to get methyl ester of O-methyl derivative (Scheme-III). The ester is hydrolyzed and converted to benzylamide via mixed anhydride technique. The amino group protection is removed by hydrogenation and converted to lacosamide by acetylation using acetic anhydride. Overall yield of lacosamide by this route is 43.6%. This route is not commercially viable as it requires column chromatography in the amide intermediate (IV) isolation stage.

Scheme-III

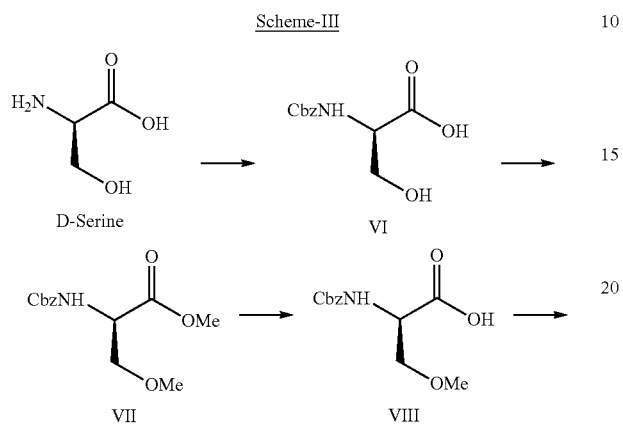

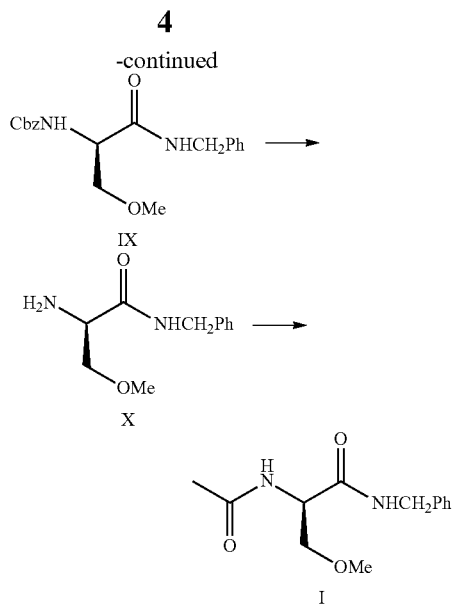

Slight variations of the process discussed in above Scheme-III are disclosed in Tetrahedron: Asymmetry 1998, 9, 3841-3854 (Scheme-IV).

Scheme-IV

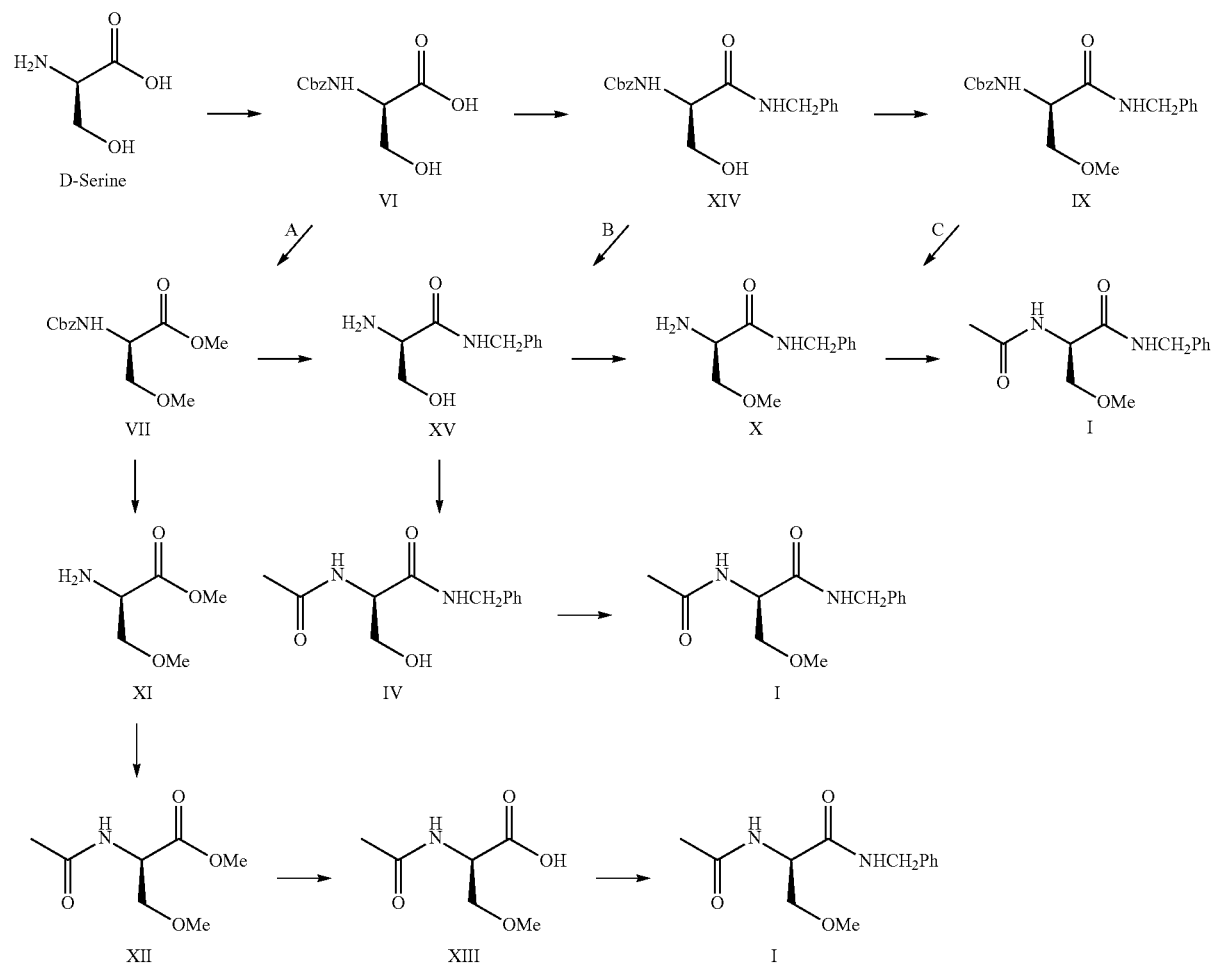

According to one variation (A) in this report N-protected D-serine is reacted with methyl iodide to get O-methyl methyl ester compound of formula-VII. Compound of formula-VII is hydrogenated, N-acetylated, ester group hydrolyzed, and amidated with benzyl amine to get lacosamide of formula-I. Overall yield of lacosamide by this route is 37.3%. Lacosamide produced by this method contained about 15% of chiral impurity. Therefore, this route is not viable on commercial scale. In the second variation (B), N-protected D-serine is reacted with benzylamine to get the amide of formula-XIV. Compound of formula-XIV is hydrogenated, N-acetylated, and O-methylated to get lacosamide of formula-I. Overall yield of lacosamide by this route is 43.7%. This route is not commercially viable as it requires chromatography technique for purifications intermediate of formula-XIV. Lacosamide produced by this method contained no chiral impurity. In the third variation (C), compound of formula-XIV is O-methylated, hydrogenated and N-acetylated to get lacosamide of formula-I. Overall yield of lacosamide by this route is 50.8%. Lacosamide produced by this method contained no chiral impurity. This route is not viable on commercial scale as it requires chromatographic technique for purifications of some of the intermediates involved in the process.

An improved process for the preparation of lacosamide is disclosed in WO2006037574 (equivalent US application No. 2008027137). In this disclosed method D-serine is N-protected with Boc group and O-methylated with methylating agents such as methyl iodide and dimethyl sulphate (Scheme-V). The resultant compound of formula-XVII is reacted with benzylamine to get the corresponding amide of formula-XVIII. N-deprotection of Boc group from compound of formula-XVIII gave the compound of formula-X which on acetylation gave lacosamide of formula-I. Overall yield of lacosamide by this route is 43.7%. This route is not commercially viable as some of the intermediates involved in the process are liquids, which makes it difficult to purify them.

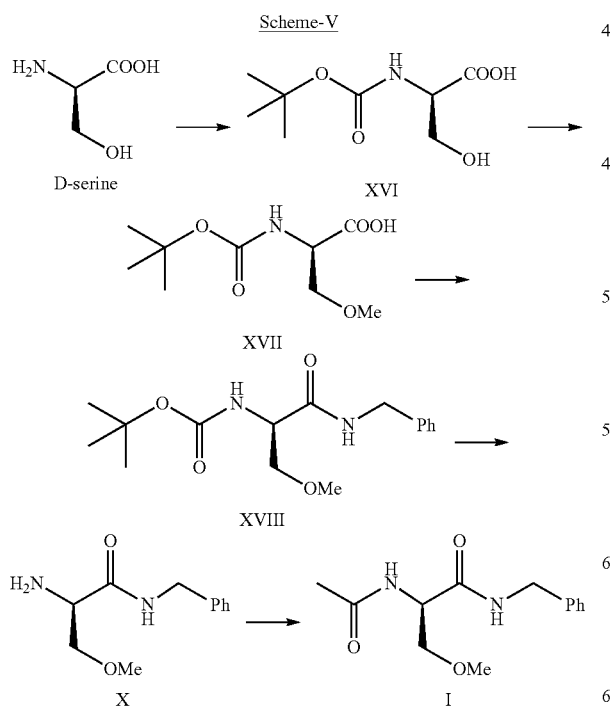

A novel process for the preparation of lacosamide is also disclosed in Bioorg. Med. Chem. 2008, 16, 8968-8975 starting from methyl ester of D-serine (Scheme-VI). Methyl ester of D-serine is converted to an aziridine intermediate of formula-XIX. N-acetylation of compound of formula-XIX followed by ring opening with methanol in the presence of an acid catalyst gave the compound of formula-XII. Ester hydrolysis of compound of formula-XII followed by reaction with benzylamine using DMTMM (4-(4,6-dimethoxy-1,3,5-triazin-2-yl)-4-methylmorpholinium chloride) gave lacosamide of formula-I. This route is not commercially viable as it requires usage of costly reagents like DTPP, DMTMM, lithium hydroxide, and $BF_3$ etherate.

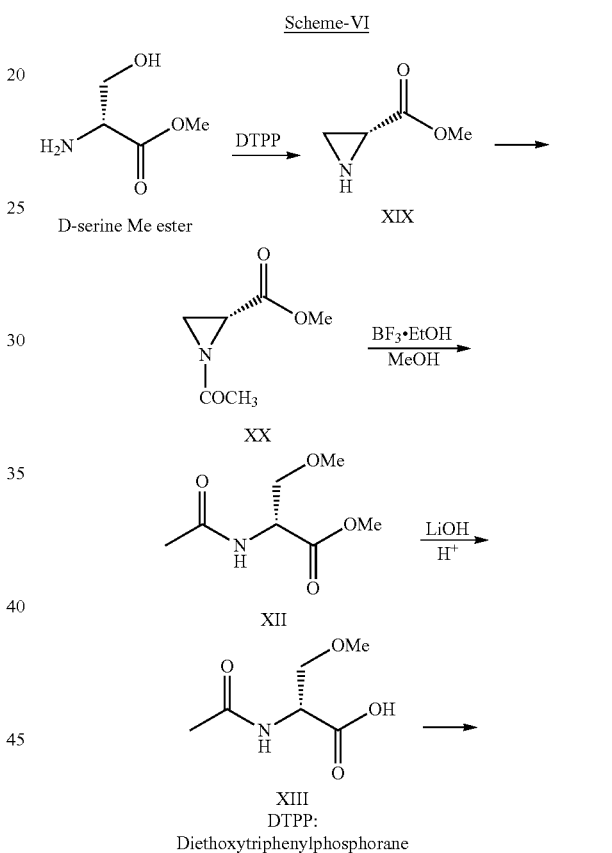

A process for the preparation of lacosamide is disclosed in US patent application No. 20090143472 using trityl group for N-protection of D-serine (Scheme-VII). In this process costly and polluting reagents like trimethylsilyl chloride, trityl chloride, hexamethyldisilazine, sodium hydride, methyl iodide were used. Therefore, this route is not commercially viable.

Scheme-VII

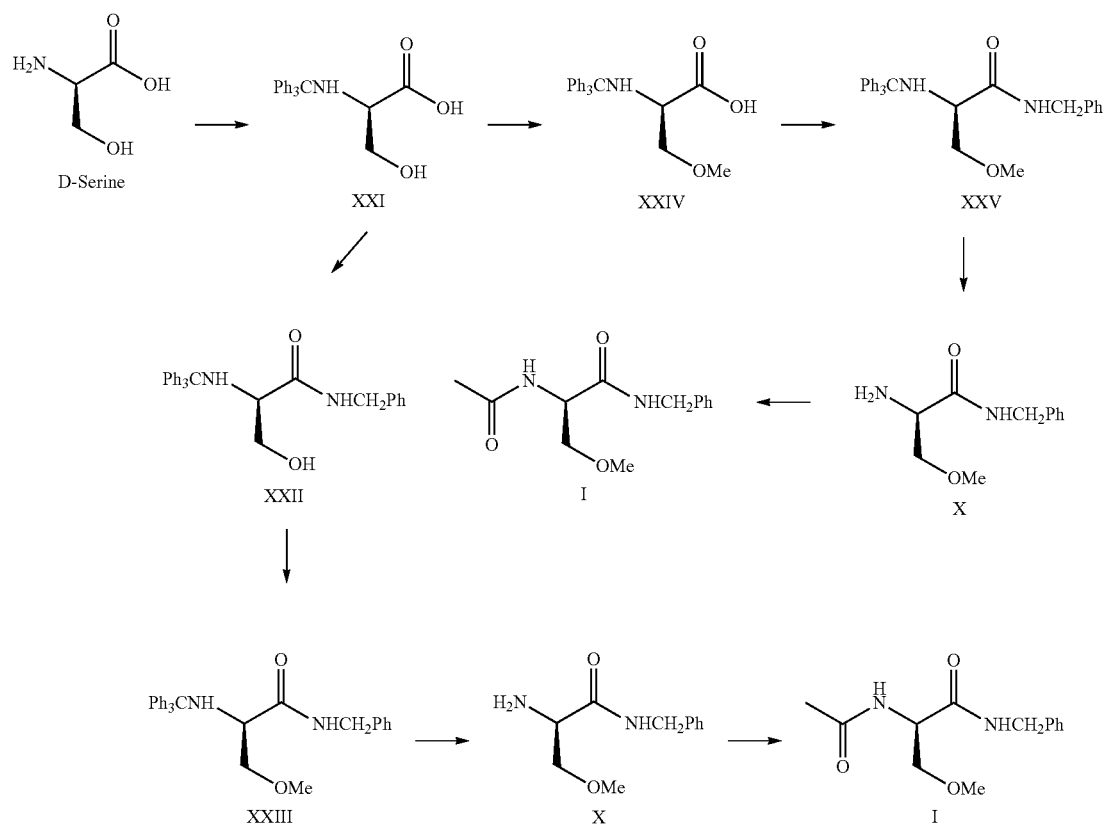

A process for the preparation of lacosamide is also disclosed in IPCOM #000181080D. In this disclosure phthalimido group is selected for N-protection of D-serine (Scheme-VIII).

We observed that a promising approach for a process for the preparation of lacosamide would be to (a) avoid the usage of costly and difficult to handle reagents; (b) avoid usage of chromatography technique; (c) and avoid Scheme-VIII

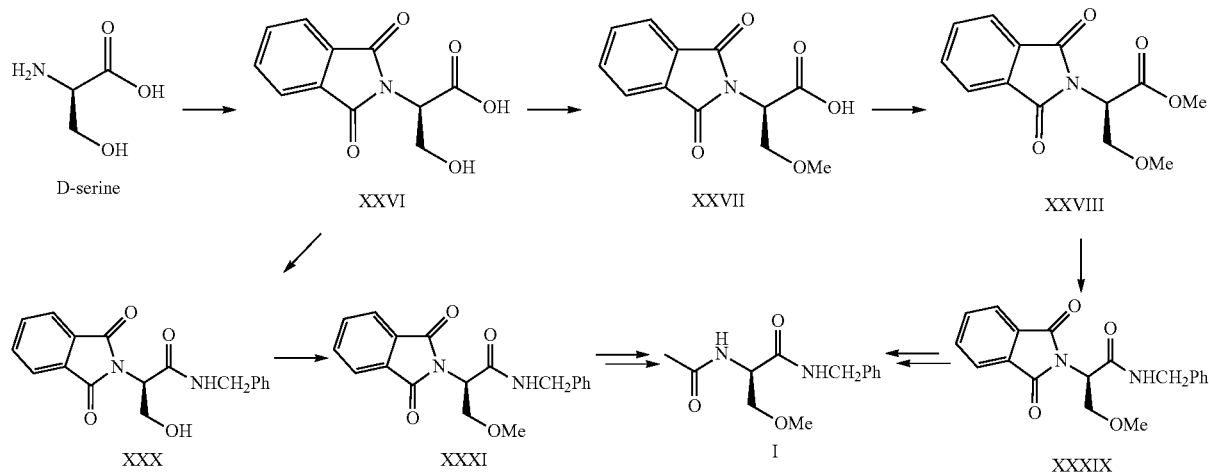

Keeping in view of the difficulties in commercialization of the above-mentioned processes for the preparation of lacosamide, we aimed to develop a simple and economical process for commercial production of lacosamide.

the preparation of liquid intermediates at late stage of the synthesis.

Accordingly, the main objective of the present invention is to provide an improved process for the preparation of lacosamide, which is commercially applicable.

Another objective of the present invention is to provide an improved process for the preparation of lacosamide avoiding the formation of liquid intermediates at late stage of the synthesis.

PROCESS OF THE PRESENT INVENTION

The present invention has been developed based on our finding that the N-deprotection of compound of formula-XVII would give (R)—O-methylserine. Acetylation of this intermediate would give (R)—O-methyl-N-acetylserine. Amidation of this intermediate with benzylamine would give lacosamide of formula-I. From the literature search it is found that (R)—O-methylserine and (R)—O-methyl-N-acetylserine are crystalline solids. Process of the present invention is as given in Scheme-IX.

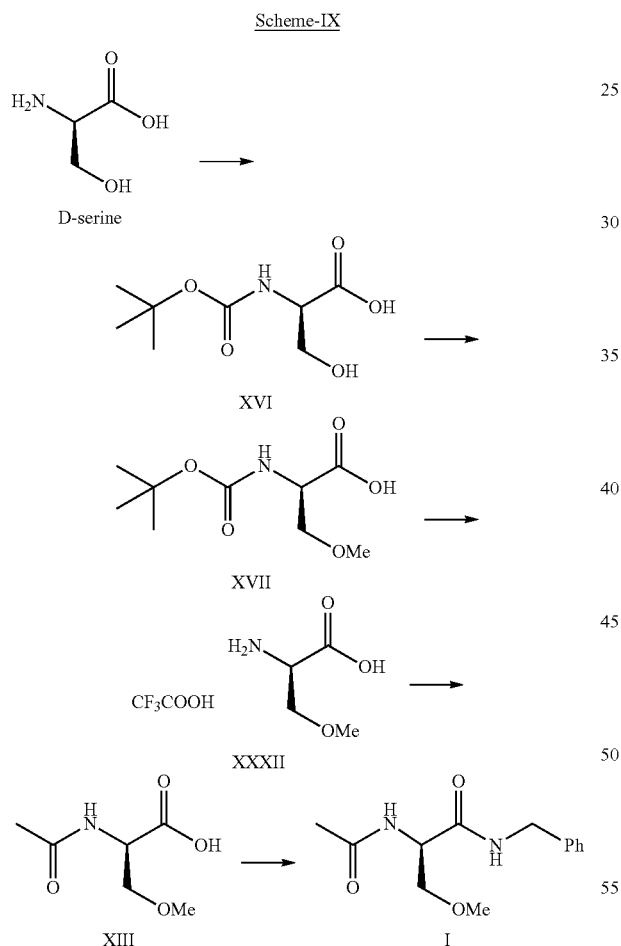

Processes disclosed in the prior art (CN101591300A) for the preparation of compound of formula-XXXII require costly reagents like sodium hydride, methyl iodide, and uses environmentally unfriendly solvents such as N,N-dimethylformamide or dimethyl sulfoxide.

Accordingly, process of the present invention provides an improved process for the preparation of lacosamide of formula-I,

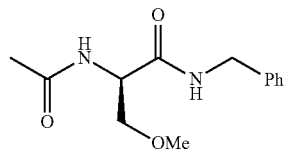

which comprises:
1. reaction of D-serine with Boc anhydride in the presence of a base in aqueous medium to get N-Boc derivative of formula-XVI,

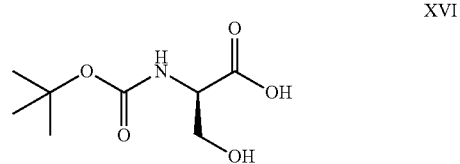

2. reaction of N-Boc derivative of formula-XVI with dimethyl sulphate in the presence of a base in aqueous medium to get the compound of formula-XVII,

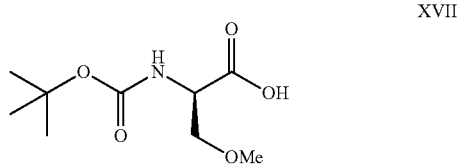

3. reaction of compound of formula-XVII with trifluoroacetic acid to get the novel trifluoroacetate salt of (R) O-methylserine of formula-XXXII,

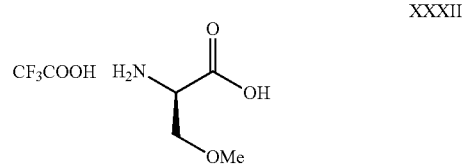

4. acetylation of compound of formula-XXXII with acetic anhydride or acetyl chloride to get the compound of formula-XIII,

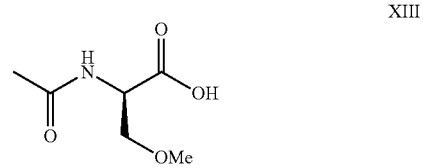

5. amidation of compound of formula-XIII with benzylamine via mixed anhydride method to get crude lacosamide of formula-I,

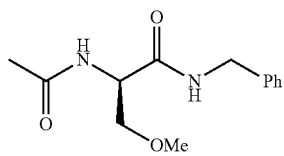

6. recrystallization of crude lacosamide from a solvent to get pharmaceutically acceptable grade lacosamide.

In a preferred embodiment of the present invention D-serine is reacted with Boc anhydride in aqueous alkali medium at 0-30° C. In the prior art (Organic Syntheses, Coll. Vol. 7, page 70 (1990)) process for the N-protection of D-serine or any other amino acid with Boc anhydride is performed in water medium along with water soluble solvents such as t-butanol, THF, dioxane, methanol, acetonitrile, dimethylformamide, etc. In the process of present invention no organic solvent is used for the preparation of N-Boc-D-serine. Amount of base used is 2-3 equivalents to D-serine. Amount of Boc anhydride used in this reaction is 1.0-1.6 equivalents to D-serine. The base used in this step is selected from sodium or potassium hydroxide, carbonate, bicarbonate, etc., preferably sodium or potassium hydroxide, more preferably sodium hydroxide. Concentration of base used is 3-6 M in water. Process of the present invention does not require any organic solvent for conversion of D-serine to N-Boc D-serine. Also, the same reaction mass can be used for methylation using dimethyl sulphate as methylating agent. In methylation step no phase transfer catalyst is required as mentioned in the prior art (WO2006037574). Also, no organic solvent is required. Compound of formula-XVII formed in the reaction can be isolated after neutralization and extraction into an organic solvent. Overall yield of compound of formula-XVII from D-serine is more than 90%.

Compound of formula-XVII is hydrolyzed with trifluoroacetic acid at 0-30° C. to get O-methyl-D-serine trifluoroacetate of formula-XXXII. The reaction can be done with or without an organic solvent. Product formed in the reaction mass is isolated by direct filtration of reaction mass or after partial concentration. Yield of O-methyl D-serine trifluoroacetate is quantitative.

Compound of formula-XXXII is acetylated using acetic anhydride or acetyl chloride in an organic solvent in the presence or absence of a catalyst such as 4-dimethylaminopyridine (DMAP) to get compound of formula-XIII. Temperature of the reaction can be in the range of 0-40° C., preferably 20-30° C. Preferred acylating agent is acetic anhydride. Preferred solvent is ethyl acetate, toluene, methylene chloride, etc. The product formed in the reaction is isolated by simply distilling of solvent. Traces of acetic anhydride present in the mass can be removed by stripping with methanol. Product is formed in quantitative yield.

Compound of Formula-XIII is reacted with an alkyl chloroformate such as methyl chloroformate, ethyl chloroformate, isobutyl chloroformate in the presence of a tertiary amine such as N-methylmorpholine, triethylamine, diisopropylethylamine at −40 to 20° C. to get a mixed anhydride of the formate. The in situ formed formate mixed anhydride is reacted with benzylamine in the presence of same base at −40° C. to 25° C. to get lacosamide of formula-I. Solvent of the reaction is toluene, ethyl acetate, cyclohexane, heptane, etc., preferably toluene or ethyl acetate. The crude product obtained from the reaction mass can be recrystallized from a number of organic solvents such as ethyl acetate, toluene, methyl isobutyl ketone, acetone, etc. to get pharmaceutically acceptable grade lacosamide. Overall yield of lacosamide from compound of formula-XIII is more than 70%.

Lacosamide produced by the process of present invention contains less than 0.1% of chiral isomer. It is suitable for formulations in treatment of central nervous system disorders.

The details of the invention are given in the Examples given below which are provided to illustrate the invention only and therefore should not be construed to limit the scope of the present invention.

EXAMPLES

Example 1

Preparation of N-Boc-O-methyl-D-serine: Into a 2 L, four-necked RB flask was charged 90 ml of water and 40 g of sodium hydroxide. D-Serine is added to the solution at 20-25° C. Boc anhydride (150 g) is slowly added to the reaction mass keeping the temperature below 20° C. The reaction mass was allowed to reach 25-30° C. and maintained for 16 h. TLC of the reaction mass showed the presence of D-serine content at <1.0% level. The reaction mass is cooled to 0-5° C. and started the simultaneous addition of aqueous sodium hydroxide (104 g of sodium hydroxide dissolved in 100 ml of water) and dimethyl sulphate (300 g) through addition funnels keeping the temperature below 5° C. The reaction mass was maintained at same temperature till the completion of reaction. The reaction mass is diluted with water and extracted the product into diisopropyl ether. Aqueous layer is neutralized with citric acid to get <3.5 pH. The reaction mass is extracted with diisopropyl ether and distilled of solvent to get 87 g of title compound as an oil.

Example 2

Preparation of O-methyl-D-serine trifluoroacetate salt: Into a 1 L, four-necked, RB flask was charged 330 ml of diisopropyl ether and 78 g of N-Boc-O-methyl-D-serine. The reaction mass was cooled to <5° C. and added 400 g of trifluoroacetic acid. The reaction temperature was allowed to reach 25° C. and maintained for 20 h. Solvent and excess trifluoroacetic acid was distilled of from the reaction mass under vacuum at 60° C. The residue was crystallized from ethyl acetate/diisopropyl ether and filtered to get 50 g of O-methyl-D-serine trifluoroacetate salt as white crystalline solid. M. R.: 228-230° C. IR (KBr): 3415, 3133, 2980, 2932, 1726, 1680, 1646, 1560, 1425, 1366, 1256, 1210, 1184, 1125, 964, 842, 798, 726 and 514 cm$^{-1}$. $^1$H-NMR (400 MHz, DMSO-d$_6$): 7.81 (broad s, exch. with D$_2$O, COOH and NH$_2$), 3.79 (t, J=4.4 Hz, 1H, CH), 3.66 (d, J=4.8 Hz, 2H, CH$_2$), 3.38 (s, 3H, OMe). $^{13}$C-NMR (100 MHz, DMSO-d$_6$): 169.06, 158.29 (q, J=31.3 Hz, CF$_3$COOH), 117.20 (q, J=297.6 Hz, CF$_3$), 70.11 (OCH$_3$), 58.50 (OCH$_2$), 52.80 (CHCOOH): EI-MS: 121 (M+2), 120 (M+1), and 88 (M−OCH$_3$).

Example 3

Preparation of N-acetyl-O-methyl-D-serine: Into a 1 L, four-necked, RB flask was charged 500 ml of ethyl acetate and 50 g of O-methyl-D-serine trifluoroacetate salt. The reaction mass was cooled to 0-5° C. and added acetic anhydride (43.8 g). The reaction mass was stirred at 25° C. for 20 h and cooled to 0-5° C. After stirring for 1 h reaction mass was filtered and washed the wet cake with 50 ml of ethyl acetate.

The wet solid was dried at 60° C. to get 40 g of N-acetyl-O-methyl-D-serine as white crystalline solid.

Example 4

Preparation of lacosamide: Into a 2 L, four-necked RB flask was charged 1250 ml of ethyl acetate and 25 g of N-acetyl-O-methyl-D-serine under nitrogen atmosphere. The reaction mass was cooled to −20° C. and added 16.5 g of N-methylmorpholine. Isobutyl chloroformate (22.3 g) was slowly added to the reaction mass. After stirring for 30 min benzylamine (17.5 g) was slowly added to the reaction mass and stirred for 30 min. Temperature of the reaction mass was raised to 25-30° C. and stirred for 1 h. Reaction mass was quenched with 100 ml of 1N HCl and transferred into a separating funnel. Organic layer was washed with brine and dried over sodium sulphate. Solvent was partially distilled of from the mass under vacuum. The residue was kept under stirring and filtered the solid. The wet solid was recrystallized from ethyl acetate to get 35 g of pharma grade lacosamide. Chiral HPLC purity is >99.9% and the related impurities are <0.5%.

ADVANTAGES OF PRESENT INVENTION

1. Present process uses cheap and readily available raw materials.
2. Present process avoids the usage of phase transfer catalysts in methylation step.
3. Present process utilizes high purity crystalline solids such as compound of formulae-XXXII and XII for making lacosamide.
4. Lacosamide produced by the process of present invention is free of chiral impurity.
5. Present process is shorter, simpler, and free from usage of hazardous reagents.
6. Present process is economically and commercially viable.

We claim:
1. Improved process for the preparation of lacosamide of formula-I,

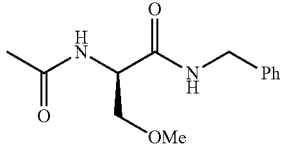

which comprises:
(i) reaction of D-serine with Boc anhydride in the presence of a base in aqueous medium at −10 to 30° C. to get N-Boc derivative of formula-XVI,

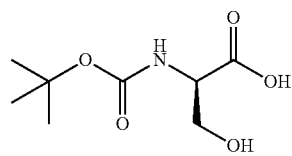

(ii) reaction of N-Boc derivative of formula-XVI with dimethyl sulphate in the presence of a base in aqueous medium at 0-30° C. to get the compound of formula-XVII,

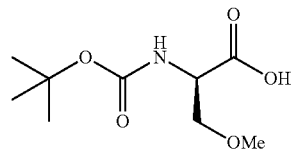

(iii) reaction of compound of formula-XVII with trifluoroacetic acid at 0-60° C. to get the novel trifluoroacetate salt of O-methyl-D-serine of formula-XXXII,

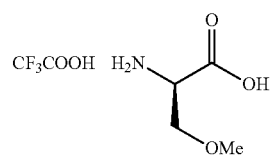

(iv) acetylation of compound of formula-XXXII with acetic anhydride or acetyl chloride to get the compound of formula-XIII,

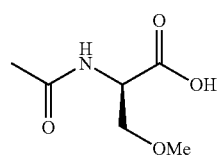

(v) amidation of compound of formula-XIII with benzylamine via a carbamate intermediate at −100 to 35° C. to get crude lacosamide of formula-I,

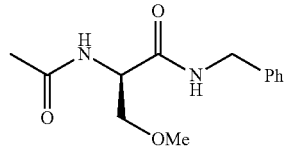

(vi) recrystallization of crude lacosamide from a solvent to get pharmaceutically acceptable grade lacosamide.

2. The process according to claim 1 wherein the base used in step (i) is selected from sodium or potassium hydroxide, carbonate, bicarbonate, etc., preferably sodium or potassium hydroxide, more preferably sodium hydroxide.

3. The process according to claim 1 wherein the amount of base used in step (i) is selected from 2-3 equivalents to the amount of D-serine.

4. The process according to claim 1 wherein the base used in step (ii) is selected from sodium or potassium hydroxide, carbonate, bicarbonate, etc., preferably sodium or potassium hydroxide, more preferably sodium hydroxide.

5. The process according to claim 1 wherein the acid used for neutralization of base in step (ii) is selected form organic acid such as acetic, propionic, oxalic, citric acid or a mineral acid such as hydrochloric acid, hydrobromic acid, sulfuric acid, phosphoric acid, preferably citric acid or sulfuric acid.

6. The process according to claim 1 wherein the solvent used for extraction of compound of formula-XVII in step (ii) is selected from ethers such as diethyl ether, diisopropyl ether, methyl isobutyl ether, methyl tert-butyl ether, esters such as ethyl acetate, isopropyl acetate, halogenated solvents such as methylene chloride, chloroform, hydrocarbon solvents such as cyclohexane, toluene, preferably ethyl acetate or diisopropyl ether.

7. The process according to claim 1 wherein the mole equivalents of trifluoroacetic acid used in step (iii) is 5 to 20 moles equivalents, preferably 10 mole equivalents.

8. The process according to claim 1 wherein the mole equivalents of acylating agent used in step (iv) is 1 to 5 mole equivalents, preferably 2 mole equivalents.

9. The process according to claim 1 wherein the acylating agent used in step (iv) is acetic anhydride.

10. The process according to claim 1 wherein the preferred temperature of reaction in step (v) is −40 to 30° C., more preferably −20 to 30° C.

11. The process according to claim 1 wherein the solvent used in crystallization of lacosamide is selected from ethers such as diethyl ether, diisopropyl ether, methyl isobutyl ether, methyl tert-butyl ether, esters such as ethyl acetate, isopropyl acetate, halogenated solvents such as methylene chloride, chloroform, hydrocarbon solvents such as cyclohexane, toluene, preferably ethyl acetate or diisopropyl ether.

\* \* \* \* \*